(12) United States Patent
Trant

(10) Patent No.: US 6,497,885 B2
(45) Date of Patent: Dec. 24, 2002

(54) METHOD AND COMPOSITION FOR IMPROVING FERTILITY HEALTH IN FEMALE AND MALE ANIMALS AND HUMANS

(75) Inventor: Aileen Sontag Trant, Mountain View, CA (US)

(73) Assignee: The Daily Wellness Company, Sunnyvale, CA (US)

( * ) Notice: Subject to any disclaimer, the term of this patent is extended or adjusted under 35 U.S.C. 154(b) by 0 days.

(21) Appl. No.: 09/742,412

(22) Filed: Dec. 22, 2000

(65) Prior Publication Data

US 2002/0122834 A1 Sep. 5, 2002

(51) Int. Cl.$^7$ .............................................. A61K 35/78
(52) U.S. Cl. ..................... 424/225; 424/729; 424/641; 424/643; 424/646; 424/682; 424/702; 514/458; 514/52
(58) Field of Search ................................ 424/725, 729, 424/641, 643, 646, 682, 702; 514/458, 52

(56) References Cited

U.S. PATENT DOCUMENTS

| | | |
|---|---|---|
| 3,970,750 A | 7/1976 | Brockemeyer et al. |
| 4,154,813 A | 5/1979 | Kleinberg |
| 4,340,592 A | 7/1982 | Adibi |
| 4,388,325 A | 6/1983 | Orzalesi |
| 4,599,232 A | 7/1986 | Bertelli |
| 4,920,098 A | 4/1990 | Cotter et al. |
| 4,954,526 A | 9/1990 | Keefer |
| 5,032,608 A | 6/1991 | Dudrick |
| 5,034,377 A | 7/1991 | Adibi et al. |
| 5,106,836 A | 4/1992 | Clemens et al. |
| 5,157,022 A | 10/1992 | Barbul |
| 5,171,217 A | 12/1992 | March et al. |
| 5,278,189 A | 1/1994 | Rath et al. |
| 5,364,644 A | 11/1994 | Walaszek et al. |
| 5,385,937 A | 1/1995 | Stamler et al. |
| 5,411,956 A | 5/1995 | Miyazaki et al. |
| 5,439,938 A | 8/1995 | Snyder et al. |
| 5,464,644 A | 11/1995 | Wullschleger et al. |
| 5,500,266 A | 3/1996 | Durnin |
| 5,523,087 A | 6/1996 | Shlyankevich |
| 5,543,430 A | 8/1996 | Kaesemeyer |
| 5,576,287 A | 11/1996 | Zaloga et al. |
| 5,576,351 A | 11/1996 | Yoshimura et al. |
| 5,594,032 A | 1/1997 | Gonzalez-Cadavid et al. |
| 5,626,883 A | 5/1997 | Paul |
| 5,631,031 A | 5/1997 | Meade |
| 5,650,418 A | 7/1997 | Rath et al. |
| 5,730,987 A | 3/1998 | Omar |
| 5,767,160 A | 6/1998 | Kaesemeyer |
| 5,780,039 A | 7/1998 | Greenberg et al. |
| 5,852,058 A | 12/1998 | Cooke et al. |
| 5,861,168 A | 1/1999 | Cooke et al. |
| 5,897,864 A | 4/1999 | Cohen |
| 5,977,073 A * | 11/1999 | Khaled |
| 6,007,824 A | 12/1999 | Duckett et al. |

FOREIGN PATENT DOCUMENTS

| | | |
|---|---|---|
| EP | 0546796 | 6/1993 |
| JP | 58-55418 | 4/1983 |
| JP | 05-163139 | 6/1993 |
| JP | 06-321786 | 11/1994 |
| WO | WO94/01006 | 1/1994 |

OTHER PUBLICATIONS

Kubo et al. J. Agric. Food Chem. (1992), vol. 40, No. 2, pp. 245–248.*

Pepeljnjak et al. Acta Pharm. (1996), vol. 46, pp. 201–206.*

Balch, James F. & Balch, Phyllis A.; Impotence, entry in Prescription for Nutritional Healing, 2nd Ed.; Copyright 1997, pp. 338–339.

Paick et al.; An experimental study of the effect of gingko biloba extract on the human and rabbit corpus cavernosum tissue; The Journal of Urology, vol. 156, Nov. 1996; pp. 1876–1880.

Internet Search Results, WedMD Health; Search Topics; "amino" amino acid; Branched–chain Amino Acids; Non-essential Amino Acids; Ginkgo; Ginseng; Protein in Diet; Want a Love Potion?; http://my.webmd.com; Jul. 23, 2001; 19 pages.

Internet Search Results, Auravita Health Channel; Search Topics: Arginine: Asian Ginseng; Dehydroepiandrosterone(DHEA); Ginkgo biliba; Impotence; www.auravita.com. Jul. 23, 2001, 17 pages.

Kaplan et al.; Safety and efficacy of sildenafil in postmenopausal women with sexual dysfunction;; Urology, vol. 53, 1999; pp. 481–486.

Article Query, Pubmed medline; Berman et al.; Effect of Estrogen withdrawal . . . (Urology, 1988); Goldstein et al., Vasculogenic female sexual dysfunction (IntJlmpotRes, 1998); Rosen et al., Effect of SSRIs on sexual function(JClin Psychphar, 1999); Pau et al., Dietary arginine . . . (JNutr. 1982) (Abstracts).

(List continued on next page.)

*Primary Examiner*—Leon B. Lankford, Jr.
*Assistant Examiner*—Susan D. Coe
(74) *Attorney, Agent, or Firm*—James Creighton Wray; Meera P. Narasimhan

(57) ABSTRACT

In a new supplemental combination, the herb, Vitex agnus-castus (chasteberry), enhances hormone balance by increasing luteinizing hormone (LH) and progesterone release and, therefore, ovulation frequency. The antioxidants, green tea, vitamin E, and selenium, improve overall reproductive health. L-arginine, an amino acid, stimulates the reproductive organs by improving circulation. Folic acid, vitamins B6 and B12, iron, zinc and magnesium help promote women's fertility.

4 Claims, No Drawings

OTHER PUBLICATIONS

Brown, Donald J. Vitex agnus castus Clinical Monograph, Townsend Letter for Doctors and Patients, Oct. 1995, pp. 138–142.

Various, Study Abstracts and Results re Vitex, Phytotherapy Research Compendium, pp. 23 and 24. 1994.

Caan et al.; Differences in Fertility Associated with Caffeinated Beverage Consumption, American Journal of Public Health, vol. 88, No. 2, Feb., 1998: pp. 270–274.

Costa et al., L-carnitine in ideopathic asthenospermia: a multicenter study, Andologia, vol. 26, Jan. 1994: pp. 155–159.

Zheng et al., Effects of Ferulic Acid on Fertile and Asthenozoospermic Infertile Human Sperm Motility, Viability, Lipid Peroxidation, and Cyclic Nucleotides, Free Radical Biology and Medicine, vol. 22, No. 4, 1997: pp. 581–586.

Kessopoulou et al., A double-blind randomized placebo cross-over controlled trial using the antioxidant vitamin E to treat reactive oxygen species associated male infertility, Fertility and Sterility, vol. 64, No. 4, Oct. 1995: pp. 825–831.

Bayer, Treatment of Infertility with Vitamin E, International Journal of Fertility, vol. 5, No. 1, Jan.–Mar. 1960: pp. 70–78.

Geva et al., The effect of antioxidant treatment on human spermatazoa and fertilization rate in an in vitro fertilization program, Fertility and Sterility, vol. 66, No. 3, Sep. 1996: pp. 430–434.

Dawson et al., Effect of ascorbic acid supplementation on the sperm quality of smokers, Fertility and Sterility, vol. 58, No. 5, Nov. 1992: pp. 1034–1039.

Scott et al., The effect of oral selenium supplementation on human sperm motility, British Journal of Urology, vol. 82, 1998: pp. 76–80.

Internet Search Results, National Library of Medicine, Search Topics: Vitamin B12 and oligospermia: Zinc sulphate and infertility: Zinc and sperm count; FOlate and human fertility, www.ncbi.nlm.nih.gov/entrez, Mar. 29, 2000–Apr. 5, 2000, 7 pages.

* cited by examiner

METHOD AND COMPOSITION FOR IMPROVING FERTILITY HEALTH IN FEMALE AND MALE ANIMALS AND HUMANS

BACKGROUND OF THE INVENTION

Because of delayed child bearing, unhealthy diets and use of tobacco, caffeine, alcohol, drugs and environmental contaminants, difficulties in conceiving have been experienced.

Needs exist for pharmaceutical compounds that improve fertility in both women and men.

SUMMARY OF THE INVENTION

This invention provides combinations of bioeffecting compounds for promoting fertility in men and women. The combinations include nutritional components that benefit fertility health. All the components have been studied separately, to determine their individual efficacy. The invention provides the first products to put these components together synergistically in women's and men's formulations.

As many as 15% of couples in the U.S. have difficulty conceiving a child. In about one third of these cases, it is the man that is infertile; in another third, the female has fertility issues. The remaining is due to a combination of male and female fertility issues, or unknown causes. In many of these cases, causes of infertility are treatable. Nutritional and lifestyle changes should be the first step to increasing chances for conception. Smoking and caffeine, drug and alcohol consumption, environmental toxicants, and stress are related to infertility in men and women. Reproductive organs are highly susceptible to free radical or oxidative damage from environmental toxicants and natural aging. A balanced, nutritional diet, and nutritional supplements with high antioxidant content can help reverse some of that damage. In women, hormone balance is critical to monthly ovulation and development of the corpus luteum (an ovarian follicle that release progesterone after release of the egg to prepare the uterus for implantation).

These and further and other objects and features of the invention are apparent in the disclosure, which includes the above ongoing written specification with the claims.

DETAILED DESCRIPTION OF THE PREFERRED EMBODIMENTS

The invention provides combinations of beneficial bioeffecting compounds for promoting fertility in women. The invention provides a scientifically validated herbal/ nutritional blend for women to improve infertility by helping to regulate the menstrual cycle and correct hormone imbalance (corpus luteum insufficiency) without increased chances of multiple births associated with drug therapy. The combination of amino acids, herbs, vitamins and minerals improves overall health and helps with many of the deficiencies that decrease fertility.

The herb, Vitex agnus-castus (chasteberry), enhances hormone balance by increasing progesterone release and, therefore, ovulation frequency. The antioxidants, green tea, vitamin E, and selenium, improve overall reproductive health. L-arginine, an amino acid, stimulates the reproductive organs by improving circulation. Folic acid, vitamins B6 and B12, iron, zinc and magnesium help promote womens' fertility.

The invention provides combinations of beneficial bioeffecting compounds for promoting fertility in men. Sperms are highly susceptible to free radical or oxidative damage from environmental toxicants and natural aging. Vitamins C and E, coenzyme Q10 and selenium are all potent antioxidants that help improve sperm counts and quality. Ferulic acid, an antioxidant found in Dong quai, also improves sperm quality. Zinc and B vitamins (B6, B12 and folate) are critical nutrients in male reproductive systems for hormone metabolism, sperm formation and motility. The amino acid, L-carnitine, promotes formation of healthy sperm.

The invention provides synergistic action of the combinations.

The two dietary supplements in male and female formulas are useful for men and women. Preferably, the distinct combinations are taken by both members of a couple in which the female age is between 21 and 46. The distinct combinations are useful for couples who have tried for 6 months or more, up to three years, to become pregnant without success. Preferably, patients take 2–4 capsules per day of the distinct formulas for three months. In women it is useful to record their basal temperature daily using thermometers and charts and to have their blood drawn for progesterone analysis at day 18–22 of the first menstrual cycle prior to taking the supplement. For men, it is useful to submit a sperm sample at the same time for analysis of count and motility. Prior to submitting sperm samples, 2–4 days abstinence is suggested for best results. No fevers over 101 degrees in the three months prior to taking the new combinations should be encountered. It is useful to repeat the analyses during the fourth menstrual cycle of the study. The first month is needed to develop baselines, followed by three months of taking the combinations product or placebo.

Preferred ranges of the combinations considered in percent by weight are:

| Components | Minimum % | Maximum % |
| --- | --- | --- |
| Women's formula | | |
| Vitex (chasteberry) | 2 | 10 |
| L-arginine | 40 | 60 |
| Green tea | 5 | 20 |
| Vitamin E | 5 | 20 |
| Selenium | .01 | 1 |
| Vitamins B6, B12 | .01 | 1 |
| Folic acid | .01 | 1 |
| Iron | .1 | 5 |
| Magnesium | 10 | 40 |
| Zinc | .1 | 5 |
| Men's Formula | | |
| L-carnitine | 40 | 70 |
| Ferulic acid in Dong Quai | .1 | 10 |
| Vitamins C and E | 10 | 40 |
| Coenzyme coQ10 | .1 | 5 |
| Selenium | .01 | 1 |
| Zinc | .1 | 10 |
| B vitamins | .001 | 1 |

Acceptable ranges of womens' and mens' formulations are:

| Components | Minimum % | Maximum % |
| --- | --- | --- |
| Women's Formula | | |
| Vitex (chasteberry) | 1 | 20 |
| L-arginine | 20 | 70 |

-continued

| Components | Minimum % | Maximum % |
| --- | --- | --- |
| Green tea | 0 | 30 |
| Vitamin E | .01 | 30 |
| Selenium | 0 | 2 |
| Vitamins B6, B12 | 0 | 2 |
| Folic acid | 0 | 2 |
| Iron | 0 | 7 |
| Magnesium | 0 | 50 |
| Zinc | 0 | 10 |
| Men's Formula | | |
| L-carnitine | 20 | 80 |
| Ferulic acid in Dong Quai | 0 | 20 |
| Vitamins C and E | .01 | 40 |
| Coenzyme coQ10 | .01 | 10 |
| Selenium | 0 | 3 |
| Zinc | 0 | 15 |
| B vitamins | 0 | 5 |

Examples of useful formulations in percent by weight are:

| Components | |
| --- | --- |
| Women's formula | |
| Vitex (chasteberry) | 5 |
| L-arginine | 50 |
| Green tea | 11 |
| Vitamin E | 11 |
| Selenium | .1 |
| Vitamins B6, B12 | .38 |
| Folic acid | .02 |
| Iron | 1 |
| Magnesium | 20 |
| Zinc | 1 |
| | 100% |
| Men's Formula | |
| L-carnitine | 60 |
| Ferulic acid in Dong Quai | 6 |
| Vitamins C and E | 30 |
| Coenzyme coQ10 | 1 |
| Selenium | .6 |
| Zinc | 2 |
| B vitamins | .4 |
| | 100% |

While the invention has been described with references to specific embodiments, modifications an variations of the invention may be constructed without departing from the scope of the invention, which is defined in the following claims.

I claim:

1. A pharmaceutical composition having fertility promoting activity in females comprising in combination components in effective amounts of Vitex agnus-castus (chasteberry), antioxidants, L-arginine, folic acid, vitamin B6, vitamin B12, iron, zinc, and magnesium;

wherein the antioxidants are selected from the group consisting of green tea, vitamin E, selenium, and combinations thereof.

2. The pharmaceutical composition of claim 1, wherein the components are present in the proportion in parts by weight of about 2 to 20% Vitex agnus-castus (chasteberry), about 5 to 50% antioxidants selected from the group consisting of green tea, vitamin E, selenium, and combinations thereof, about 10 to 80% L-arginine, about 0.001 to 1% folic acid, about 0.001 to 1% vitamin B6 and vitamin B12, about 0.1 to 10% iron, about 0.1 to 10% zinc, and about 5 to 50% magnesium.

3. A supplement, comprising a herb, Vitex agnus-castus (chasteberry)for-enhancing fertility, increasing progesterone release and ovulation frequency, antioxidants, green tea, vitamin E, and selenium for improving reproductive fertility, L-arginine, an amino acid for stimulating reproductive organs by improving circulation, folic acid, vitamins B6 and B12, iron, zinc and magnesium for promoting women's fertility.

4. A supplement having fertility promoting activity in females comprising in combination components in effective amounts of Vitex agnus-castus (chasteberry), antioxidants, L-arginine, folic acid, vitamin B6, vitamin B12, iron, zinc, and magnesium as a treatment for promoting fertility activity in females;

wherein the antioxidants are selected from the group consisting of green tea, vitamin E, selenium, and combinations thereof.

* * * * *